United States Patent [19]

Basham

[11] 3,996,922

[45] * Dec. 14, 1976

[54] FLEXIBLE FORCE RESPONSIVE TRANSDUCER

[75] Inventor: Raymond B. Basham, Fort Worth, Tex.

[73] Assignee: Electronic Monitors, Inc., Fort Worth, Tex.

[ * ] Notice: The portion of the term of this patent subsequent to Sept. 25, 1990, has been disclaimed.

[22] Filed: May 19, 1975

[21] Appl. No.: 578,883

Related U.S. Application Data

[60] Division of Ser. No. 389,268, Aug. 17, 1973, Pat. No. 3,898,981, which is a continuation-in-part of Ser. No. 176,983, Sept. 1, 1971, Pat. No. 3,760,794, which is a continuation-in-part of Ser. No. 97,737, Dec. 14, 1970, abandoned.

[52] U.S. Cl. .................................. 128/2 R; 128/2 S; 128/DIG. 29; 179/111 E; 307/88 ET
[51] Int. Cl.² ............................................ A61B 5/08
[58] Field of Search ........ 128/2 S, DIG. 29, 2.05 E; 179/111 E; 307/88 ET

[56] References Cited

UNITED STATES PATENTS

| | | | |
|---|---|---|---|
| 3,354,373 | 11/1967 | Fatovic | 307/88 ET X |
| 3,736,436 | 5/1973 | Crites | 307/88 ET |
| 3,760,794 | 9/1973 | Basham | 128/2 R |
| 3,786,495 | 1/1974 | Spence | 179/111 E X |
| 3,809,828 | 5/1974 | Haugsjaa et al. | 179/111 E X |
| 3,890,511 | 6/1975 | Haugsjaa et al. | 179/111 E X |
| 3,894,243 | 7/1975 | Edelman et al. | 179/111 E X |
| 3,926,177 | 12/1975 | Hardway, Jr. et al. | 128/2 S |

OTHER PUBLICATIONS

*Bell Laboratories Record*, Mar. 1973, p. 94.

*Primary Examiner*—Kyle L. Howell
*Attorney, Agent, or Firm*—Richards, Harris and Medlock

[57] ABSTRACT

Apparatus for monitoring the respiration of a patient through utilization of a force responsive transducer, which ideally is a capacitor transducer constructed from alternate layers of conductive and nonconductive materials that are flexible such that when placed beneath a patient or a resilient patient support, such as a mattress, the distance between the plates of the transducer changes for the purpose of producing electrical responses that upon amplification energize indicator means, such as a visual alarm or an audible alarm. The transducer is responsive to the vertical, reciprocating forces and motions caused by respiration and along with the associated circuitry, is sufficiently sensitive to energize an alarm upon sensing a cessation of respiration.

4 Claims, 12 Drawing Figures

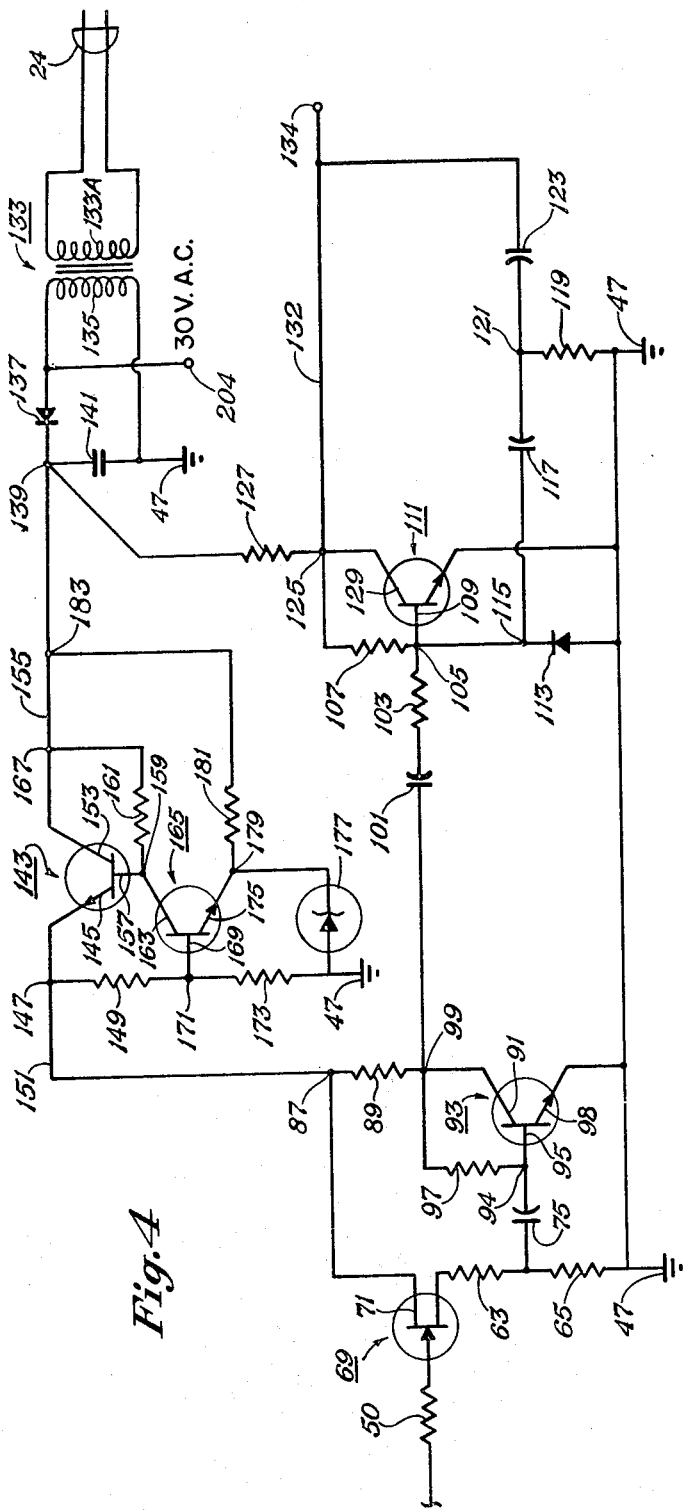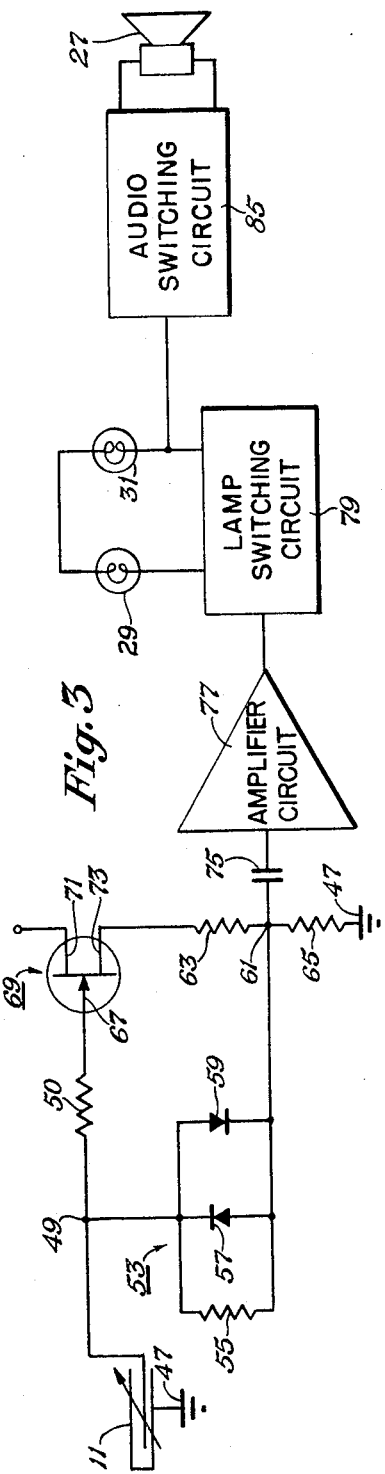

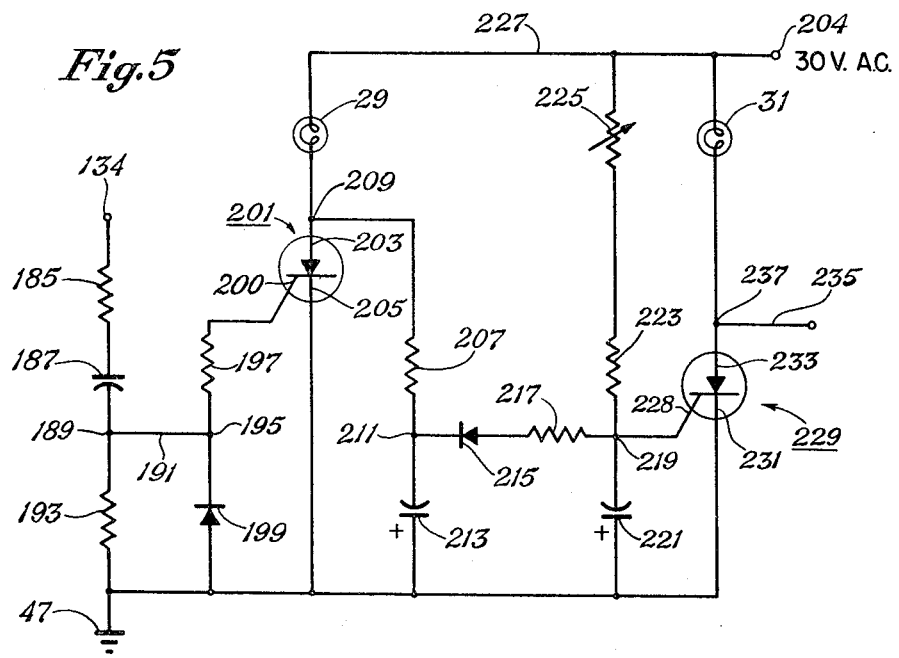
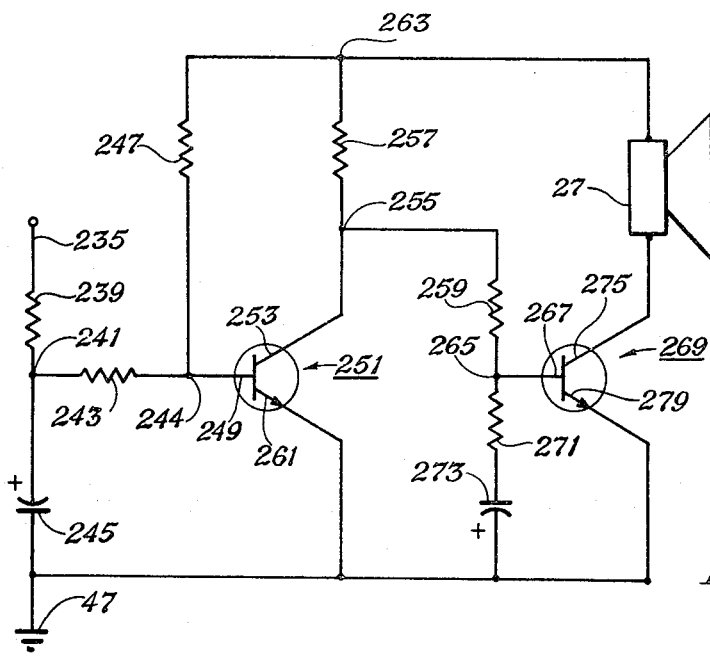

FLEXIBLE FORCE RESPONSIVE TRANSDUCER

This is a division of application Ser. No. 389,268, filed Aug. 17, 1973, now U.S. Pat. No. 3,898,981; which is a continuation-in-part of application Ser. No. 176,983, filed Sept. 1, 1971, now U.S. Pat. No. 3,760,794; which was a continuation-in-part of application Ser. No. 97,737, filed Dec. 14, 1970, now abandoned.

This invention relates in general to patient monitoring apparatus, particularly to apparatus adapted to monitor respiration for the purpose of providing an alarm upon cessation of respiration.

A number of different types of methods and apparatus have been proposed in the past for the purpose of monitoring respiration. However, the previously known apparatus and methods have not yet received widespread acceptance due to a number of severely limiting disadvantages. One previously known method utilizes the connection of electrodes directly to the skin of a patient to sense electrical resistance changes during respiration in the skin surrounding the expanding and retracting chest cavity. Connecting electrodes directly to the patient is often irritating to the patient, whose skin frequently rejects the saline solution commonly used to produce satisfactory contact with the electrode and the patient. And in addition, such method can be dangerous if a large voltage is applied inadvertently or accidentally across electrodes secured to a patient. A number of accidents of this type have been reported. In addition, devices have been proposed for sensing force of motion cessation that include the use of a photoelectric cell, but such devices lack that degree of sensitivity leading to successful operation.

The invention provides improved respiration monitoring apparatus that accurately senses respiration and cessation of respiration without need for direct attachment to the body.

The invention provides respiration monitoring apparatus that utilizes a capacitor transducer for accurately sensing respiration and cessation of respiration. The invention also provides apparatus for respiration monitoring that utilizes electrical responses from a capacitor transducer, that amplifies such responses, and that transmits the responses to either an audible or visual indicator and cicuit means to notify a patient's attendant that respiration has ceased.

The invention comprises respiration monitoring apparatus, the apparatus including a force responsive transducer, which ideally is a capacitor transducer with movable plates, adapted for placement beneath a patient or a patient support such as a mattress. The transducer senses changes in the forces and movements caused by patient respiration. By suitably amplifying the electrical responses generated with the transducer, these responses may be fed to indicator means that provide either a visual or an audible warning that signifies when the electrical responses cease due to cessation of respiration. The indicator means are ideally a lamp, for visual warning and an audible device such as a speaker, for audible warning, to signify the cessation of electrical response. Such apparatus and method are sufficiently sensitive and accurate to sense cessation in the generally vertical, reciprocating forces generated by patient breathing. Hence, should this bodily function cease, the visual and audible alarms are energized.

In one embodiment a memory device is provided that continuously indicates that temporary cessation had occurred in the event that the patient recovers and begins breathing again.

For a more complete understanding of the present invention and for further objects and advantages thereof, reference may now be had to the following description taken in conjunction with the accompanying drawings in which:

FIG. 3 is an electrical schematic diagram showing a preferred circuit for energizing both a visual and an audible alarm to indicate cessation of respiration.

FIG. 4 is an electrical schematic diagram of an amplifier circuit shown in block form in FIG. 3.

FIG. 5 is an electrical schematic diagram of a lamp switching circuit shown in block form in FIG. 3.

FIG. 6 is an electrical schematic diagram of an audio switching circuit shown in block form in FIG. 3.

Figure 1:
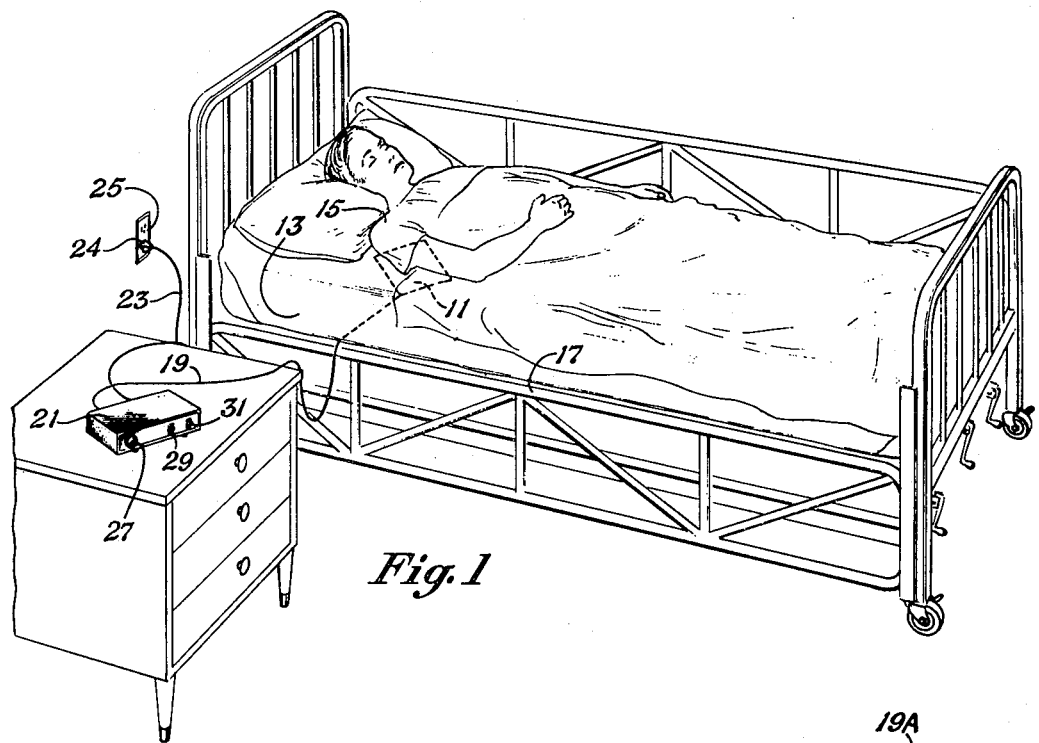
FIG. 1 is a perspective view of respiration monitoring apparatus positioned relative to a patient lying in a conventional hospital bed in accordance with the principles of my invention.

Referring initially to FIG. 1 of the drawing, the numeral 11 designates a force responsive transducer inserted between the mattress 13 and springs (not shown), generally under the shoulder region of a patient 15 in a reposed position in a conventional hospital bed 17. The force responsive transducer 11 is connected by a coaxial cable 19 with a console 21, which is in turn connected by multi-line conductor 23 and plug 24 with a wall socket 25 associated with a 110 volt alternating current source. As shown in FIG. 1, the console 21 has exposed on its exterior an audible alarm 27 and two visual alarms 29, 31, the operation and function of which will be explained subsequently.

Figure 2:
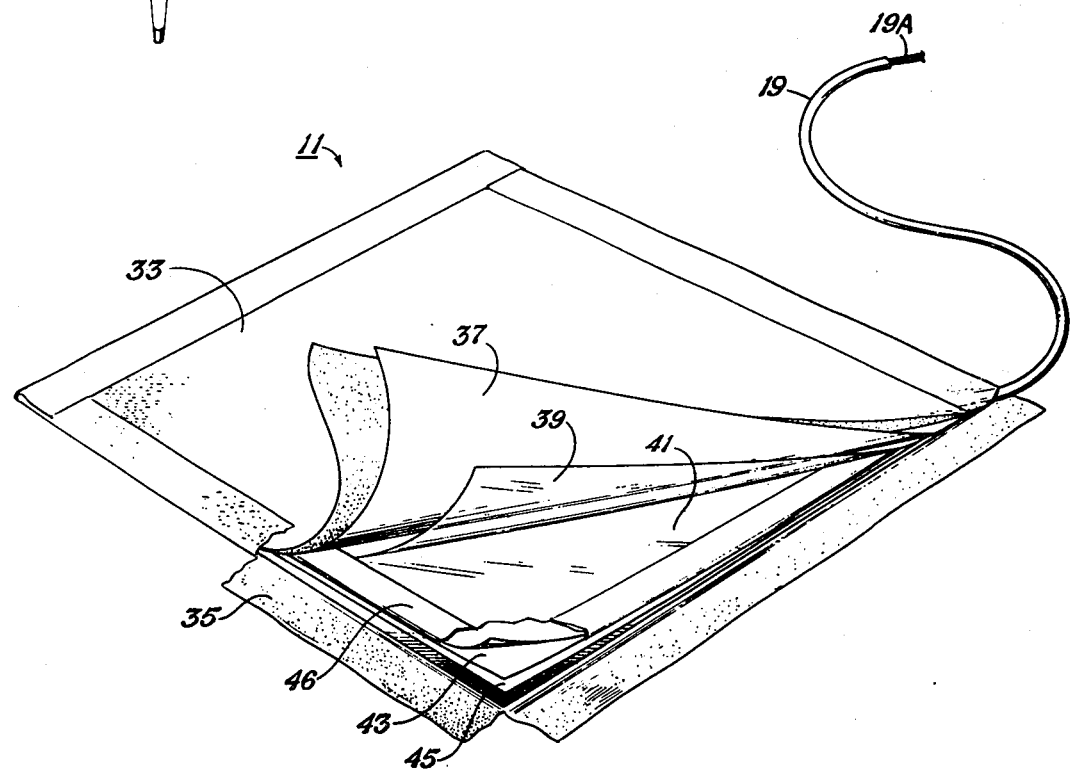
FIG. 2 is a perspective view of a force responsive transducer, with portions thereof separated to show the construction thereof.

Referring to FIG. 2, the force responsive transducer 11 is preferably a capacitor transducer comprised of layers of flexible, alternately conductive and nonconductive material as follows. The exterior of the capacitor 33 is of a nonconductive material such as preferably a vinyl or also an acrylic or cellulose, the lower side of such covering material having a flap 35 adapted to fold over and bond to the upper cover. As shown in FIG. 2 the next material from the top is preferably a flexible conductive sheet 37 of suitable material such as sheet steel that is adjacent a nonconductive sheet of material 39 that in turn lies adjacent a conductive sheet 41 on top of a nonmetallic sheet 43 adjacent an exterior conductive sheet 45 that is covered by material 33, as previously explained. The sheets 39, 41 and 43 are secured in this instance with a nonconductive strip 46. The outer conductive sheets 37 and 45 not only provide the reference plates to establish capacitance with respect to the inner plate 41 but also shield the inner plate from stray electric fields.

Figure 7:
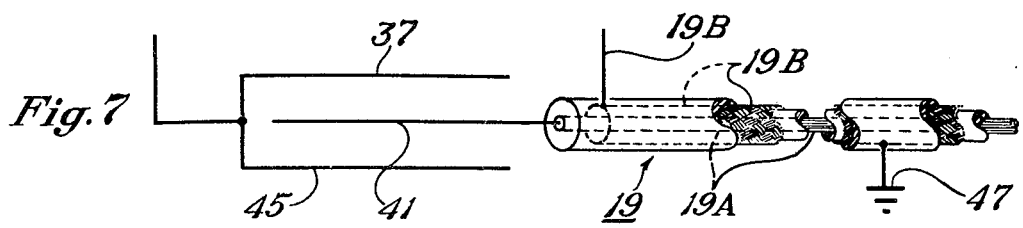
FIG. 7 illustrates in more detail the manner in which electrical connections are made to the transducer.

The coaxial cable 19 leading from the transducer to the console 21 has its center conductor 19A connected to the conductive sheet 41 as illustrated in FIG. 7. The shield 19B of cable 19 is connected to the two outer conductive sheets 37 and 45 as illustrated by connection 19B'. At the console the shield 19B is grounded as illustrated at 47. An example of a satisfactory conductive material is sheet steel metal of about 0.003 inch thickness, while a satisfactory nonconductive material is acrylic having a thickness of approximately 0.003 of an inch. The alternate layers of conductive and nonconductive material may be approximately 6 inches square. Hence, the composite transducer has the characteristics of flexibility and pliability for the purpose of accurately sensing force changes upon the mattress 13.

Referring initially to FIG. 3, which is a schematic diagram of a preferred circuit means, the numeral 11 designates the variable capacitor transducer illustrated in FIGS. 2 and 7. The cable conductor 19A is connected with the juncture 49 of a resistor 50 and a protective network 53 that comprises in this instance a biasing resistor 55 connected in parallel with diodes 57, 59, which are in turn connected with the juncture 61 of two source resistors 63 and 65, 65 being connected with ground 47 as shown.

Resistor 50 is connected with the gate 67 of a field effect transistor 69 having its drain 71 connected with a 25 volt source received from a 110 volt AC source, as will be explained in connection with FIG. 4. The source 73 of the transistor 69 is connected in series with the source resistor 63.

The juncture 61 between source resistors 63 and 65 is connected with a capacitor 75, in turn connected in series with an amplifier circuit means 77 that feeds first a lamp switching circuit 79 for selective activation of two lamps 29, 31 (see also FIG. 1) or other suitable visual indicators, and second an audio switching circuit 85 that drives a speaker 27 (see also FIG. 1).

Describing the FIG. 3 circuit operationally, the field effector transistor 69 is connected in a source follower configuration with the resistors 63 and 65, which are connected with the source, in this instance the variable capacitor 11. The resistor 63 supplies the bias to regulate the gate cut-off point on the field effect transistor. The voltage developed across resistor 65 is supplied back to the capacitor 11 through resistor 55, and polarizes the capacitor transducer in such a way that it will act upon this voltage but will produce a variable voltage that is inversely proportional to the change in the capacitance of the transducer. This variable voltage is then sensed through resistor 50 by the gate 67 of the field effect source follower. The output of the field effect source follower is transmitted to the juncture 61 of resistors 63, 65, which are connected through capacitor 75 to the amplifier. In operation each time pressure is applied to the capacitor transducer 11, a signal appears at the output of the amplifier circuit 77. The resulting amplified signal is applied to the lamp switching circuit 79. The respiration lamp 29 responds to cyclic breathing pressure applied through the mattress 13 to the transducer. This lamp is adapted to flash each time there is breathing motion applied to the capacitance transducer by the mattress. So long as the cyclic mattress motion caused by patient breathing continues, the respiration lamp 29 will continue to light cyclically.

In the event of respiration failure of the patient, the respiration lamp will extinguish and after a period of time determined by the setting of adjustable resistor 225, the alarm lamp 32 will switch on. This in turn applies an AC signal into the audio switching cicuit 85, which in turn closes the switching circuit in order to excite an audible alert device that can be a buzzer, but preferably is a solid state transistor signaling device that gives an audible alarm simultaneous with the emergency lamp.

Referring to FIG. 4, for an explanation of a preferred amplifier circuit, the drain 71 of the field effect transistor 69 is connected at the juncture 87 of a resistor 89 which is connected in series with the collector 91 of a transistor 93. The base 95 of the transistor 93 is connected with the juncture 94 between the output of capacitor 75 and a resistor 97, the collector 91 being connected with the juncture 99 between resistors 89 and 97. The emitter 98 of transistor 93 is connected to ground. The juncture 99 is connected with a capacitor 101 connected in series with a resistance 103, which in turn is connected at the juncture 105 of a resistor 107 and the base 109 of a transistor 111.

The juncture 105 and the base 109 of transistor 111 are connected with a diode 113 through a juncture 115 leading to a capacitor 117. A resistor 119 is connected with ground and with the juncture 121 between capacitor 117 and a capacitor 123, which is in turn connected with the juncture 125 between resistance 127 and the collector 129 of transistor 111, such juncture also connecting resistors 107 and 127 as shown. Resistor 127 is connected at a terminal 139 and thus across an unregulated 35 volts (DC). The conductor 132 and terminal 134 define the output of the amplifier circuit.

The 35 volt source is derived typically from a plug 24 of a 110 volt AC source that is connected across the primary 133A of a transformer 133, the secondary 135 that in turn is connected through a rectifier, which in this instance is a diode 137 connected between the juncture 139 between resistor 127 and capacitor 141 connected to ground as shown.

A regulator circuit comprises a transistor 143 having its emitter 145 connected at a juncture 147 between resistor 149 and a conductor 151 leading to the juncture 87 between resistor 89 and the field effect transistor 69. The collector 153 of transistor 143 is connected with the 35 volt unregulated supply via conductor 155, and its base 157 is connected with the juncture 159 of a resistor 161 and the collector 163 of a transistor 165. The opposite terminal 167 of resistor 161 is connected with the conductor 155 and thus the 35 volt unregulated source. The base 169 of transistor 165 is connected to the juncture 171 between resistors 149 and 173. The emitter 175 of transistor 165 is connected with the cathode of a Zener diode 177, the anode of such diode being connected to ground and to resistor 173 as shown. In addition, the cathode of the Zener diode 177 is connected with the juncture 179 between a resistor 181 and the emitter 175 of transistor 165. The resistor 181 is connected at terminal 183 with the conductor 155 leading to the 35 volt source.

The regulator circuit shown is of conventional form, using a 15 volt Zener diode as a reference and a voltage divider device transistor 165 which in turn controls the base of the transistor 143, the output of the regulator then being the reference voltage difference in the voltage divider defined by resistors 149 and 173 for setting the bias operating point for transistor 165, which would be the 25 volt point plus the forward voltage drop across transistor 165.

Operationally, the above-described amplifier circuit consists of two stages, that include respectively transistor 93 and transistor 11, having their capacitance coupled. Transistor 111 has a low pass filter of the negative feed-back type connected between the collector and the base of transistor 111. This filter consists of capacitors 117, 123 and resistor 119. This network provides a necessary frequency feed-back in order to give the amplifier relatively low frequency roll off so that any signals above and higher than the frequency of normal respiration signals are rejected, and the gain of the amplifier is thus extreme for such signals.

A preferred lamp switching circuit is illustrated in FIG. 5 with the output 134 of the amplifier circuit being connected in series with a resistor 185 and a capacitor 187, which is connected at the juncture 189 between a conductor 191 and a resistor 193 leading to ground 47. Conductor 191 leads to the juncture 195 between a resistor 197 and a diode 199, also connected with ground. The output of resistor 197 is connected with the gate 200 of a silicon controlled rectifier 201 having its anode 203 connected in series with the lamp 29, which is connected with the 30 volt source 204 as shown, the cathode 205 of the rectifier being connected with ground.

The anode 203 of rectifier 201 is connected through a juncture 209 with a resistor 207 in turn connected through a juncture 211 between a capacitor 213 that is grounded as shown. The diode 215 is connected in series with a resistor 217, which is connected with the juncture 219 between a capacitor 221, connected with ground, and a resistor 223 connected in series with a variable resistor 225 connected to the 30 volt AC source applied to the conductor 227.

The gate 228 of a silicon controlled rectifier 229 is connected with the juncture 219 between capacitor 221 and resistors 217, 223, while the cathode 231 is connected to ground and the anode 233 is connected with the lamp 31 and with a lamp 29 through conductor 227. An output conductor 235 leads from the juncture 237 between lamp 31 and the anode 233 of the rectifier 229.

Operationally, the respiration lamp switching circuit 79 comprises the silicon controlled rectifier 201 that switches the lamp 29 on each time there is a respiration signal from the transducer 11. The anode 203 of the rectifier 201 is connected to the capacitor 213 in order to maintain a charge on this capacitor so that the emergency lamp 31 will remain off during the time that the charge is maintained. Each time rectifier 201 is energized and the respiration lamp 29 is turned on there is a negative voltage appearing at the anode 203 of the rectifier 201, and this in turn maintains a negative charge on capacitor 213.

With respect to rectifier 229, the emergency lamp switching rectifier, would normally keep the emergency light 31 energized if it were not for the negative charge maintained on the capacitor 213. Failure of patient respiration or a failure of the respiration lamp 29 would no longer maintain a negative charge on capacitor 213, and thus, the emergency lamp 31 would be excited. As a consequence, that in the event of failure of the respiration light 29, the instrument will give alarm. Such a malfunction energizes the emergency lamp 31 and the audible alarm (as explained subsequently) so that the patient attendant would know that there was either an emergency or there had been a failure of the instrument. Any failure in the circuitry described thus far will energize lamp 31; this in turn tends to make the whole instrument essentially fail safe.

A preferred audio switching circuit is illustrated in FIG. 6, in which a resistor 239 is connected with the output 235 of the lamp switching circuit and with a juncture 241 between resistor 239 and a capacitor 245 connected to ground. The resistor 243 is connected with the juncture 244 between a resistor 247 and the base 249 of a transistor 251, having its collector 253 connected with the juncture 255 between a resistor 257 and a resistor 259, and its emitter 261 connected to ground as shown. Resistor 247 and resistor 257 are connected with a juncture 263 leading to the 35 volt DC source.

Resistor 259 is connected with the juncture 265 between a base 267 of a transistor 269 and a resistor 271 connected in series with a capacitor 273 connected with ground. The collector 275 of transistor 269 is connected to the speaker 27 connected with the 35 volt DC source at junction 263, while the emitter 279 of the transistor is connected to ground.

Operationally, the output of the emergency switch devices (transistor) 229 of FIG. 5 charges capacitor 245 through lamp 31. When the lamp 31 is switched on, it produces a negative charge on capacitor 245 that biases the transistor 251 in the cut-off condition so that its collector is at its maximum voltage. Under these conditions a positive bias is supplied to the base of transistor 269, which switches on the transistor and in turn causes current to flow through an audible alert device such as speaker 27. When the emergency lamp 31 is in the off condition, there is no charge applied to the capacitor 245, such that transistor 251 is biased in the forward direction through resistor 247. This in turn drops the base current to zero in transistor 269, which in turn cuts off this transistor to prevent current flow to the audio alert device.

In hospitals, where a plurality of the devices of the present invention may be employed simultaneously to monitor the breathing of a plurality of newborn babies respectively, means are needed to allow an attendant nurse to know if a given baby has experienced temporary cessation of breathing but has subsequently recovered. For example, while the nurse is attending to one baby, a baby behind her may experience temporary cessation of breathing causing the lamp 31 of its associated monitor to be energized and its alarm 27 to sound. By the time the nurse turns around, breathing may be restored causing the monitor lamp 31 to turn off and the alarm 27 to terminate its sounding. Thus, the nurse will not be able to know which baby had temporary problems from observing the monitors employed.

Figure 8:
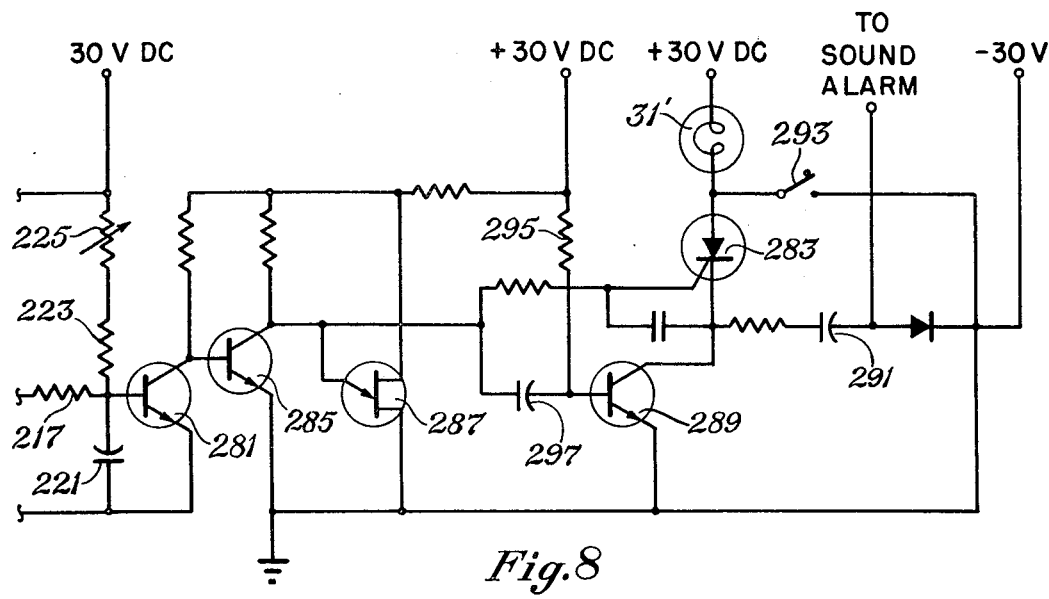
FIG. 8 is an electrical schematic diagram of an alternative warning system incorporating a memory device.

Referring to FIG. 8, there will be described a circuit arrangement incorporating a memory device which will retain evidence of cessation of breathing if it occurs by the baby being monitored by a given monitor. This circuitry is a modification of that of FIG. 5 with additional components employed. In this respect, transistor 281 is substituted for silicon controlled rectifier 229 and the lamp 31 removed from the position shown in FIG. 5. The lamp is connected as shown at 31' in FIG. 8 to a silicon controlled rectifier 283 which is employed for memory purposes. The remainder of the circuitry of FIG. 8 comprises a transistor 285, a unijunction transistor 287, a transistor 289 and a capacitor 297. Transistor 287 and capacitor 297 form an oscillator. Normally when a patient is breathing, transistor 281 is in a nonconductive state, transistor 285 is conducting, unijunction transistor 287 is off or in a nonconducting state, silicon controlled rectifier 283 is off or in a nonconducting state and transistor 289 is conducting. Thus, lamp 31' is off and the sound or audible alarm 27 coupled between the silicon controlled rectifier 283 and transistor 289 also is off. When transistor 281 is off, a positive bias is applied to the base of transistor 285 maintaining it in a conductive state. The resulting low potential from the collector of transistor 285 maintains the transistor 287 in a nonconducting state. The transistor 289 is biased to a conducting state through resistor 295.

When a patient stops breathing, transistor 281 becomes conductive thereby causing transistor 285 to become nonconductive. This causes the oscillator to begin oscillating for the production of positive pulses which are applied to the gate of silicon controlled rectifier 283 and negative pulses which are applied to the base of transistor 289. The first positive pulse applied to the gate of silicon controlled rectifier 283 renders it in a continuous conduction state while each negative pulse applied to the base of transistor 289 renders it temporarily nonconducting. Thus, since silicon controlled rectifier 283 is on and transistor 289 is turned on and off, lamp 31' periodically is energized to flash on and off. As the lamp 31' flashes on and off, a negative pulse periodically is applied to the sound alarm 27 by way of capacitor 291 to periodically turn the sound alarm on and off also. If the patient begins to breath again transistor 281 is turned off, transistor 285 turned on which terminates oscillation of oscillator 287. Thus, transistor 289 becomes conductive continuously again. Silicon controlled rectifier 283 also remains in a conductive condition thereby continuously energizing the lamp 31' providing a memory or continuous record to allow the attendant to know from an inspection of the lamp 31' that the patient had a temporary cessation of breathing. In order to return the lamp 31' and silicon controlled rectifier 283 to their normal conditions, the attendant merely has to temporarily close switch 293 to ground the anode circuit of the silicon controlled rectifier 283 in order to place the rectifier in its normal nonconducting state.

Figure 9:
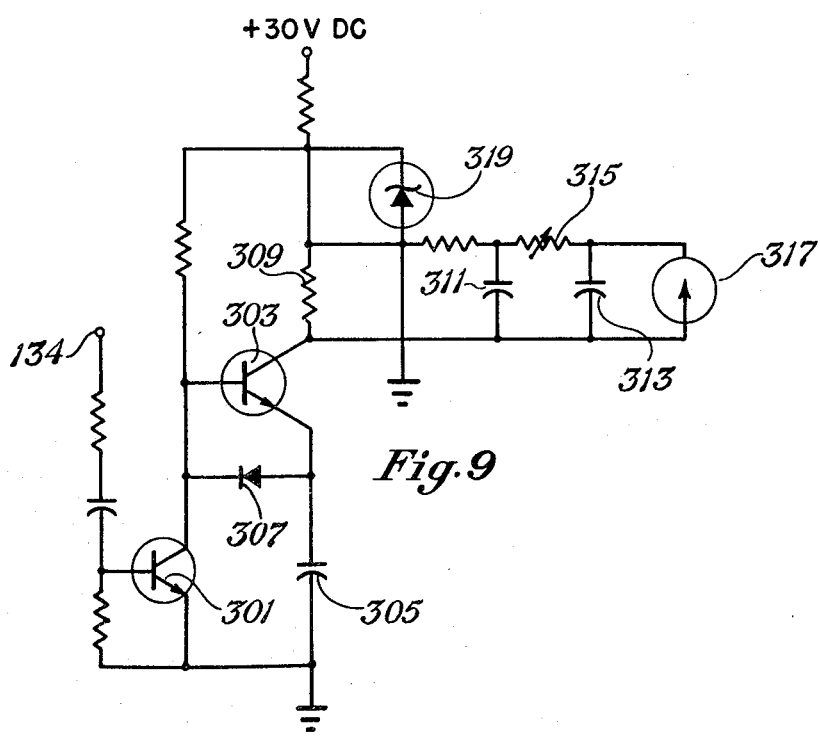
FIG. 9 is an electrical schematic diagram of a rate meter for indicating the rate of respiration of a patient.

Referring to FIG. 9, there is disclosed circuitry and a device which may be employed as a visual indicator of breathing in addition to the lamp 29. This circuitry comprises a rate meter and may be coupled to the amplifier of FIG. 4 at terminal 134. In the circuitry of FIG. 9, transistor 301 normally is off but is turned on each time respiration occurs. Transistor 303 normally is on when there is no respiration but becomes nonconductive when transistor 301 becomes conducting. A capacitor 305 is charged through transistor 303 when it is conducting and transistor 301 is off. When transistor 301 conducts, the capacitor 305 is discharged through diode 307 and transistor 301. When this occurs, transistor 303 is cut off by the fact that its base is more negative than its emitter. When transistor 301 turns off, transistor 303 simultaneously turns on in order to charge the capacitor 305 and the charging current is measured across resistor 309 by way of an integrator comprising capacitors 311 and 313 and variable resistor 315, the latter of which is adjusted or calibrated whereby the respiration rate of the patient may be measured. The Zener diode 319 is provided in order to regulate the voltage that is supplied to the capacitor 305 in order that the voltage supplied to it is a very accurate reference voltage.

From the above apparatus and operational descriptions, it should be apparent that I have provided an invention having significant advantages. By placing the force responsive transducer beneath the patient as shown in FIG. 1, the respiration of the patient may be sensitively monitored. The transducer is sensitive to the generally vertical, reciprocating motions transmitted to the mattress 13 by the patient's respiration. As a consequence, should the patient's respiration be interrupted, the visual and audible alarms associated with the console will be energized for the purpose of alerting the patient's attendant. For the first time an apparatus has been provided that possesses sufficient sensitivity to monitor accurately respiration without requiring direct attachment to the patient.

Figure 10:
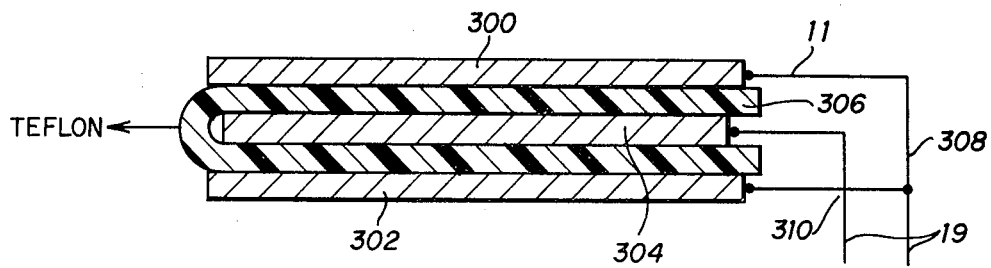
FIG. 10 is a schematic in section of an alternate embodiment of a force responsive transducer using an electret of a synthetic resin polymer sheet.

Referring to FIG. 10, there is shown an alternate embodiment of the force responsive transducer 11 including electrically conductive sheets 300 and 302 as electrodes of a transducer with an electrically conductive sheet 304 as a center electrode. Folded around the center electrode 304, between the electrodes 300 and 302, is a charged synthetic resin polymer film 306, for example a charged film of Teflon.

As explained with reference to the transducer of FIG. 2, the outer electrodes 300 and 302 are interconnected to a single line 308 and the center electrode 304 is singly connected to a line 310, with both the lines 308 and 310 forming the electrical conductor 19 connected as shown in FIG. 3.

Enclosing the structure of FIG. 10 is the covering material as illustrated in FIG. 2, such as a vinyl material 33. In a typical embodiment of the transducer of FIG. 10, each of the electrodes 300, 302 and 304 are flexible steel sheets and the film 306 is Teflon having a thickness of 2 mils and a volume resistivity greater than $10^{18}$ ohm-centimeters, a dielectric strength of 430 volts/mil, and a dielectric constant of 2. Typically, the film 306 is approximately 5 inches by 10 inches and when folded around the electrode 304 provides a transducer approximately 5 inches square.

The synthetic resin polymer film 306 carries a permanent electrical polarization or high voltage between opposite surfaces thereof. Thus, the surface of the film 306 juxtaposition the electrodes 300 and 302 may contain a positive polarity and the surface juxtaposition the center electrode 304 a negative polarity to provide an electric field across the film.

In operation of the transducer of FIG. 10, it is placed to respond to the respiration rate of a patient. The normal breathing motion of the patient produces a varying applied force against the electrodes 300 and 302. An increasing force causes the electrodes 300, 302 and 304 to be moved nearer the electrically polarized film 306 and thereby moving an electrical conductor through an electric field and a current flows in the electrodes and through the conductor 19 to the circuitry of FIG. 3. The current flow in the conductor 19 varies with the force applied to the electrodes 300 and 302 which in turn varies with respiration respiraion rate of a patient.

Figure 11:
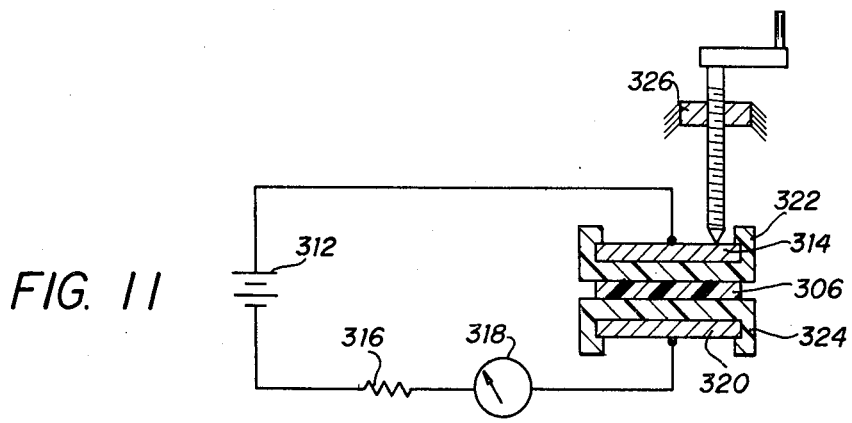
FIG. 11 is a schematic of a circuit and charging fixture for developing an electrostatic charge in a synthetic resin polymer sheet.

Referring to FIG. 11, there is shown circuitry and a fixture for developing an electrostatic charge in the synthetic resin polymer film 306. A voltage source 312 is connected to an electrode 314 and to a current limiting resistor 316. The resistor 316 is in series with a meter 318 having one terminal connected to an electrode 320. Adjacent the electrode 314 is a plastic sheet 322, for example, a 2 mil thick film of Mylar. Similarly, a plastic sheet 324 is adjacent the electrode 320. Between the plastic sheets 322 and 324 is the synthetic resin polymer film 306. A clamp mechanism 326 is illustrated in contact with the electrode 314 to apply a pressure thereto to sandwich the resin polymer film 306 tightly between the plastic sheets 322 and 324 during the charging operation.

Figure 12:
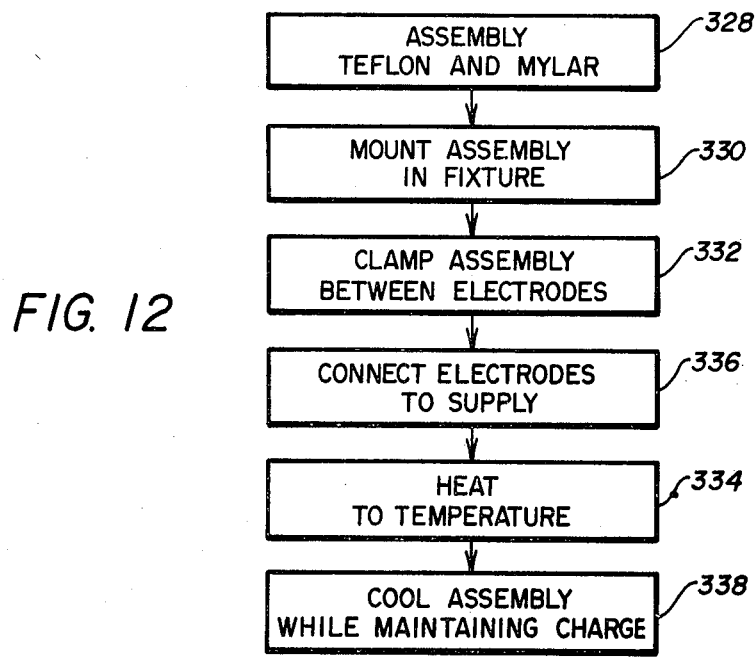
FIG. 12 is a block diagram flow chart illustrating the steps of charging a synthetic resin polymer sheet for use in an electret force responsive transducer.

Referring to FIG. 12, there is shown a flow chart of a process for charging a synthetic resin polymer film with the system of FIG. 8. Initially, the plastic sheets 322 and 324 are fastened to metal plate electrodes 314 and 320, respectively, and the resin polymer film 306 assembled between the plastic sheets to form a sandwich configuration in a step 328. Typically, the plastic sheets 322 and 324 and the polymer film 306 are 2 mils thick. Dimensionally, the plastic sheets extend beyond the outer limits of the polymer film 306 and are folded around the metal plate electrodes. After assembling the plastic sheets and the polymer, this sandwich configuration is mounted between the electrodes 314 and 320 in the step 330. Next, in a step 332, the sandwich assembly is clamped tightly between the electrodes 314 and 320 by means of the clamp 326. With the synthetic resin polymer sheets and the plastic sheets now clamped between the electrodes 314 and 320 the entire assembly is connected to the voltage supply 312 as during the step 336. Next, the assembly is placed in an oven and heated to a predetermined temperature in a range from 275° F. to 325° F. during a step 334. This heating raises the temperature of the polymer film 306 such that the material more readily accepts a polarized condition. This polarizes an electrostatic charge on the polymer film 306 through the plastic sheets 322 and 324 to a level as determined by the source 312 and the resistor 316. For example, the source 312 provides a 2500 volt potential across the electrodes 314 and 320 at a current as indicated by the meter 318 of 50 micro amperes.

To maintain a polarized condition on the synthetic resin polymer film 306, a volume resistivity on the order of $10^{18}$ ohm-centimeters is required. To provide the desired polarized condition to the polymer film 306, the plastic sheets 322 and 324 have a volume resistivity of $10^{16}$ ohm-centimeters. These plastic sheets function to isolate the porous resin polymer film 306 from the electrodes 314 and 320 when in a heated condition for charging.

Following the step 336, the entire assembly, while connected to the source 312, is cooled to ambient temperature during a step 338. This cooling step, with the source connected, sets the electrostatic charge on the film 306.

While the invention has been shown in several of its forms, it should be apparent to those skilled in the art that it is not so limited but is susceptible to various changes and modifications without departing from the spirit thereof. The specific form of force responsive transducer is not limited specifically to the capacitor transducer shown and described, and the configuration of the capacitor transducer itself may be varied widely within the broad scope of the invention. In addition, the invention is not limited in its broadest sense to the specific form of circuitry shown by way of preferred embodiment, since there are alternate circuit configurations capable of producing the intended, satisfactory result.

What is claimed is:

1. A flexible force responsive means for placement beneath a patient or patient support for sensing the respiration of a patient, comprising in combination:
   two electrically conductive flexible metallic sheet electrodes, a center electrically conductive flexible metallic sheet electrode positioned between said two sheet electrodes,
   a synthetic resin, electrostatically charged, flexible sheet located between adjacent metallic sheets of conductive electrodes to form alternate layers with the electrically conductive sheets,
   said flexible sheets of electrically conductive material being sensitive to changes in force applied thereto and caused by the respiration of a patient,
   an electrical conductor connected to the center sheet electrode,
   an electrical conductor connected to the two outer sheet electrodes, and
   flexible nonconductive material surrounding and covering said outer electrodes of flexible sheets of conductive material.

2. The force responsive means as set forth in claim 1 wherein said synthetic resin flexible sheet has a volume resistivity not less than $10^{18}$ ohm centimeters.

3. The force responsive means as set forth in claim 1 wherein the synthetic resin flexible sheet extends beyond the outer edge dimensions of the center sheet electrode.

4. A flexible force responsive means as set forth in claim 1 wherein said two electrically conductive flexible metallic sheet electrodes extend beyond the outer edge dimensions of said synthetic resin flexible sheet to shield said flexible metallic sheet center electrode.

* * * * *